United States Patent [19]

Rechmann

[11] Patent Number: 5,762,493
[45] Date of Patent: Jun. 9, 1998

[54] HAND-HELD UNIT FOR FLUSHING THE OPERATING POINT OF A LASER LIGHT BEAM EMERGING FROM A LIGHT CONDUCTOR

[76] Inventor: Peter Rechmann, Dellestrasse 70, Duesseldorf-Unterbach, Germany, 40627

[21] Appl. No.: 648,061

[22] PCT Filed: Nov. 15, 1994

[86] PCT No.: PCT/EP94/03776

§ 371 Date: May 17, 1996

§ 102(e) Date: May 17, 1996

[87] PCT Pub. No.: WO95/13759

PCT Pub. Date: May 26, 1995

[30] Foreign Application Priority Data

Nov. 19, 1993 [DE] Germany .................. 43 39 488...4

[51] Int. Cl.[6] ........................................................ A61C 1/00
[52] U.S. Cl. .......................................... 433/29; 606/16
[58] Field of Search ................................ 433/29; 606/16

[56] References Cited

U.S. PATENT DOCUMENTS

| 4,503,853 | 3/1985 | Ota et al. ................ 606/16 |
| 5,300,067 | 4/1994 | Nakajima et al. ........ 606/16 |

FOREIGN PATENT DOCUMENTS

| 0247746 | 12/1987 | European Pat. Off. . |
| 0515983 | 12/1992 | European Pat. Off. . |
| 5317329 | 3/1994 | Japan . |

*Primary Examiner*—John J. Wilson
*Attorney, Agent, or Firm*—Diller, Ramik & Wight, PC

[57] ABSTRACT

In a hand-held unit (1) with a housing (2), with a light conductor (3) held in the housing (2), particularly for the dental treatment with laser light, and with a flushing means (4) directing liquid in the region of the operating point of the laser light beam, it is provided that the flushing means (4) produces a bundled liquid jet (6), and that the laser light beam (8) is coupled into the liquid jet (6).

12 Claims, 1 Drawing Sheet

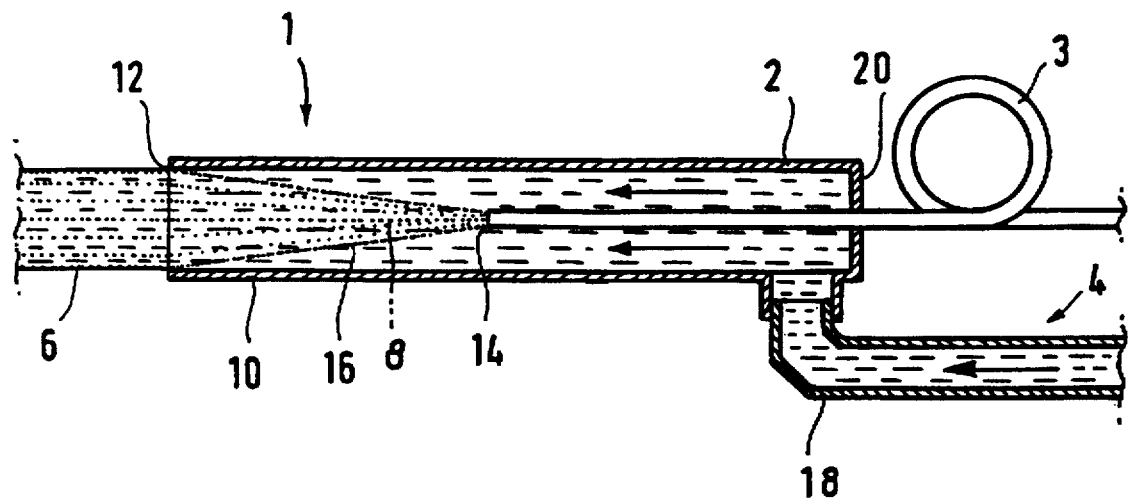

HAND-HELD UNIT FOR FLUSHING THE OPERATING POINT OF A LASER LIGHT BEAM EMERGING FROM A LIGHT CONDUCTOR

BACKGROUND OF THE INVENTION

The invention relates to hand-held units used to guide a laser light of medical apparatus, wherein, due to the heat developing at the operating point of the laser light beam, a flushing means is provided for directing a liquid onto or near the operating point of the laser light beam.

By hand-held units are meant handle pieces which permit an operator to manually guide the laser light in medical applications with a straight-lined or bent guidance of the light being possible. They also include, if need be, remote-controlled application heads for guiding the light of a laser light beam as used, for example, in urology.

Hand-held units for dental application are known, for example, from EP-0 375 578 A1, DE 3911 871 A1 or EP 0 073 617 A1.

A disadvantage with such hand-held units with spray flushing is that the flushing means may impair the effectiveness of the laser light beam in the operating point and that the cooling effect is insufficient.

Therefore, it is an object of the invention to provide a hand-held unit for guiding a light conductor as well as a process for flushing the operating point of a laser light beam emerging from a light conductor, by means of which an improved cooling of the operating point of the laser light beam is possible without impairing the effectiveness of the laser light.

SUMMARY OF THE INVENTION

The invention advantageously provides coupling the laser light beam into the liquid jet of the flushing means. Coupling the laser light beam into the liquid jet permits using the liquid jet as a light-conducting element extending the light conductor in such a manner that the laser light beam exactly follows the course of the liquid jet and the operating point of the laser light beam corresponds to the impingement point of the liquid jet. Thus, cooling is effected with high efficiency at precisely that spot where the heat develops, i.e., the operating point of the laser light beam.

A further advantage of the light-conducting liquid jet consists in that the removed substance is directly flushed away by the liquid jet. According to prior art, laser light beams not accompanied by a liquid or air jet always suffer from the problem that the crater formed in the worked substance after several laser pulses is full of removed material. The laser light beam is absorbed by the removed material and therefore being only partially effective to remove additional material. With the liquid jet and the integrated laser light beam according to the invention, the site worked by the laser light beam is continuously flushed due to the continuously supplied liquid.

The material removed by the laser light beam is also heated. The immediate transportation of the hot removed material from the operating region avoids additional undesired heating of the basic substance.

The laser light energy density remains constant over a longer liquid jet track section. Thus, it is possible to use the hand-held unit both in the contact mode and spaced from the operating point. In the contact mode, the nozzle outlet end is set directly upon the operating point. While the light conductor burns down in the contact mode when the light conductor is directly set down according to prior art, the light conductor cannot burn down because the laser light beam, according to the invention, is coupled into the liquid jet.

Preferably, the light conductor is arranged coaxially in a nozzle for the liquid jet. The nozzle bundles the liquid jet and coaxially encloses the light conductor, so that parallelism of the laser light beam and the liquid jet is ensured.

The end of the light conductor is arranged at a distance before the nozzle outlet end of the nozzle. Thus, it is ensured that the laser light beam can expand to the diameter of the liquid jet. This advantageously permits microsurgical operations upon teeth, even in the contact mode. The hand-held unit can be set directly upon the site to be worked. Also in these cases, a sufficient cooling of the site worked is ensured. The arrangement of the light conductor end within the nozzle, namely, before the nozzle outlet end, completely protects the light conductor end against burning down and mechanical destruction. Upon ablating hard substance of the tooth, extremely hard microparticles are formed which recoil onto the fiber by the ablation pressure and may damage the end of the light conductor. This also results in that the energy distribution in the emerging laser light beam may become heterogeneous. Due to the fact that, according to the invention, the end of the light conductor is arranged protected within the nozzle, no undesired burning down of the fiber end can occur.

Since the end of the light conductor is arranged at a distance before the nozzle outlet end of the nozzle, cooling of the worked surface is always ensured since the light conductor cannot directly lie on the surface to be worked.

In this case, the end of the light conductor is arranged at such a distance from the nozzle outlet end that the laser light cone emerging from the light conductor reaches the diameter of the liquid jet at the nozzle outlet end. The inner diameter of the light conductor determines the distance of the free end of the light conductor from the nozzle outlet end, the emerging laser light beam being expected to have expanded to the diameter of the liquid jet as accurately in the region of the nozzle outlet end as possible or directly therebehind in the flow direction. Within the liquid jet, the laser light beam is totally reflected at the interface between the liquid jet and the surrounding air, so that the liquid jet may serve as a light conductor.

As flushing liquid, it is also possible to use a liquid whose refractive index is adapted to the refractive index of the surface to be worked. Thus, the effectivity of the laser light beam can be increased due to the reduced reflection at the surface to be worked.

BRIEF DESCRIPTION OF THE DRAWING

The FIGURE is a schematic longitudinal cross-sectional view of the hand-held unit of the invention, and discloses a tube through which flushing liquid flows toward an outlet of the tube and which also surrounds a light conductor.

DESCRIPTION OF THE PREFERRED EMBODIMENTS

A hand-held unit 1 comprises a housing 2 which, in the schematic representation of the functional principle, forms a tube or nozzle 10 for a liquid jet 6. A cooling means 4, not shown in detail, supplies the cooled liquid jet 6 is via a connection conduit 18 of the nozzle 10 at an end opposite a tube or nozzle outlet end 12. Coaxially with the tube or nozzle 10 and sealed with respect to the housing 2 is a light conductor, e.g., a light-conducting fiber 3, which is introduced at the a front face 20 of the 2 housing opposite the nozzle outlet end 12, via which fiber a laser light beam 8 is introduced into the nozzle 10 filled by cooled flushing liquid.

The light-conducting fiber 3 ends at a distance before the nozzle outlet end 12 in the tube or nozzle 10, the end 14 of the light-conducting fiber 3 being arranged at such a distance before the nozzle outlet end 12 of the nozzle 10 that the laser light cone 16 emerging from the light-conducting fiber 3 reaches the diameter of the liquid jet 6 at the nozzle outlet end 12 or directly behind the nozzle outlet end 12 in the flow direction. The inner diameter of the light-conducting fiber 3 (which is the sine of half the emergence angle of the laser light beam 8) determines the distance of the end 14 of the fiber 3 from the nozzle outlet end 12. The emerging laser light beam 8 expands to the diameter of the liquid jet 6 as accurately in the region of the nozzle outlet end 12 as possible. Alternatively, the laser light cone 16 can also expand to the diameter of the liquid jet only immediately behind the nozzle outlet end 12 in the flow direction, so that no absorption can occur at the inner nozzle surface. At the liquid-air junction, the laser light cone 16 is totally reflected, so that the liquid jet 6 serves as an extension of the light-conducting fiber 3.

The laser light beam 8 expanded to the diameter of the liquid jet 6 retains its energy density over a longer section of the track of the liquid jet, so that the hand-held unit 1 can be used both in the contact mode and at a distance from the substance to be worked. This distance can amount to up to 50 mm and, if necessary, can be set to a predetermined distance by means of a spacer. The typical liquid jet diameter amounts to between 0.5 and 2.5 mm, preferably 1.5 mm.

The end 14 of the fiber 3 should not end too far before the nozzle outlet end 12, since the laser light beam 8 may then be reflected at the inner surface of the nozzle 10, with the laser light energy being partially absorbed. If the end 14 of the fiber 3 protrudes too far with respect to the nozzle outlet end 12, this is disadvantageous at least for the contact mode of the hand-held unit 1, since the laser light energy density is higher at the nozzle outlet end 12, i.e., within a section directly behind the nozzle outlet end 12, there are different laser light intensities, since the light cone has only expanded to the liquid jet diameter at a distance from the nozzle outlet end.

Different light conductors 3 can be used. For example, light-conducting fibers having different diameters or having a different diameter, with the fiber diameter being the same, can be used.

The flushing liquid for the liquid jet 6 is introduced into the nozzle 10 via the connection conduit 18 in such a manner that a laminar liquid flow develops within the nozzle. To this end, it may be useful to introduce the liquid into the nozzle 10 at a location other than that illustrated in the diagrammatic sketch. The flushing liquid can be supplied at a slight overpressure. A useful liquid quantity in a dental application of the hand-held unit amounts to from about 30 to 100 ml/min.

Deviating from the FIGURE, it might be useful to introduce the flushing liquid in parallel to the emerging liquid jet 6, while the flexible light-conducting fiber 3 is arcuately transferred into the coaxial position in the nozzle 10 without being led through the front face 20.

In order to obtain a laminar flow profile as ideal as possible, also means for evening out the liquid jet may be interposed between the connection conduit 18 and the nozzle 10. Furthermore, measures for reducing the friction on the inner nozzle surfaces are possible to favor the development of a laminar flow profile.

Water or a liquid whose refractive index is adapted to the refractive index of the surface to be worked can be used as a flushing liquid. This results in less reflections at the surface to be worked, e.g., tooth surface, since the reflection is proportional to the difference between the refractive indices. Here, it is to be considered that the use of a flushing liquid with another refractive index affects the expansion angle of the laser light cone 16.

The refractive index of the tooth surface (hydroxyapatite) amounts to n=1.63. When using water (refractive index n=1.34), a good approach towards the refractive index of a tooth surface is obtained. By adding calcium chloride to the flushing liquid, the refractive index can be improved to n=1.52.

A fluoride (e.g. $CaF_2$) can be added to the flushing liquid as well. Thus, the worked tooth surface would automatically be fluoridized. It has been found out that on the basis of simultaneously applying fluorides and the laser light beam, the effectivity of the fluoridation is improved and the tooth surfaces worked will be remarkably less prone to caries. This can probably be put down to the fact that laser light accelerates the chemical reaction.

A liquid-guided laser light beam is also applicable for the desensitization of dental necks in a particularly advantageous manner.

As an alternative to coupling the laser light beam 8 into the liquid jet 6 via fiber optics, it is also possible to couple the laser light beam 8 into the liquid jet 6 via another optical means. This, for example, can be realized with a lens system, it being also possible to couple the laser light beam into the nozzle 10 via an optical window and/or mirror. Conducting the laser light by means of the liquid jet 6 is particularly effective when the laser light jet 8 is not absorbed by the flushing liquid or only to a minimum degree. The best results can be achieved with flushing liquids on the basis of water with laser light of a wavelength between 300 and 700 nm, preferably between 350 and 520 nm.

For other wavelength ranges, other flushing liquids can achieve a better efficiency, e.g., organic liquid such as alkanes in the UV wavelength range, anhydrous inorganic liquids such as perhalogenated carbon compounds in the IR wavelength range.

What is claimed is:

1. A laser light unit for dental treatment comprising a housing (2) including a tube (10), said tube (10) having an outlet end (12) of a predetermined diameter, a light conductor (3) at least partially housed within said housing (2), said light conductor (3) having an output end (14) from which is generated a laser light cone (16), said output end (14) being spaced from said outlet end (12) a predetermined distance such that said laser light cone (16) diverges from said output end (14) toward and acquires substantially said predetermined diameter substantially at said outlet end (12), fluid input means (18) for imputing fluid (6) into said tube (10), and said output end (14) being located between said fluid input means (18) and said outlet end (12) whereby the laser light beam (8) and the fluid (6) exit the outlet end (12) of the tube (10) substantially coaxially.

2. The laser light unit as defined in claim 1 wherein the fluid (6) within the tube (10) exhibits laminar flow.

3. The laser light unit as defined in claim 1 wherein fluid (6) is supplied between substantially about 30 to 100 ml/min.

4. The laser light unit as defined in claim 1 wherein said predetermined diameter is between substantially about 0.5 to 2.5 mm.

5. The laser light unit as defined in claim 1 wherein said predetermined light diameter is substantially 1.5 mm.

6. The laser light unit as defined in claim 1 wherein the fluid (6) comprises substantially water.

7. The laser light unit as defined in claim 1 wherein the laser light cone (16) has a wavelength between substantially 300 to 700 nm.

8. The laser light unit as defined in claim 1 wherein the laser light cone (16) has a wavelength between substantially 350 to 520 nm.

9. The laser light unit as defined in claim 1 wherein said conductor (3) is at least partially in coaxial relationship to said tube (10).

10. The laser light unit as defined in claim 1 wherein the fluid (6) comprises substantially water and calcium chloride.

11. The laser light unit as defined in claim 1 wherein the fluid (6) comprises substantially water and fluoride.

12. The laser light unit as defined in claim 1 wherein the fluid (6) comprises substantially water and a disinfectant.

* * * * *